US00PP25521P3

(12) United States Plant Patent
Danziger

(10) Patent No.: US PP25,521 P3
(45) Date of Patent: May 5, 2015

(54) ***ANGELONIA* PLANT NAMED 'DALON12'**

(50) Latin Name: *Angelonia angustifolia*
Varietal Denomination: DALON12

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 13/986,280

(22) Filed: Apr. 18, 2013

(65) Prior Publication Data

US 2014/0317818 P1 Oct. 23, 2014

(51) Int. Cl.
*A01H 5/00* (2006.01)

(52) U.S. Cl.
USPC ..... Plt./404

(58) Field of Classification Search
USPC ..... Plt./404
See application file for complete search history.

(56) References Cited

PUBLICATIONS

Danziger Flower Farm, Sep. 26, 2012.*
UPOV Record Detail for *Angelonia angustifolia* 'DALON12' printed Jun. 3, 2014.*
UPOV Record Detail for *Angelonia bonpl* 'DALON 12' printed Jun. 3, 2014.*

* cited by examiner

*Primary Examiner* — Susan McCormick Ewoldt
*Assistant Examiner* — Keith Robinson
(74) *Attorney, Agent, or Firm* — Cassandra Bright

(57) ABSTRACT

A new and distinct *Angelonia* cultivar named 'DALON12' is disclosed, characterized by large white colored flowers. The new variety is free branching and flowering with an upright plant habit and good garden performance. The new variety is a *Angelonia*, normally produced as an outdoor garden or container plant.

2 Drawing Sheets

Figure 1:
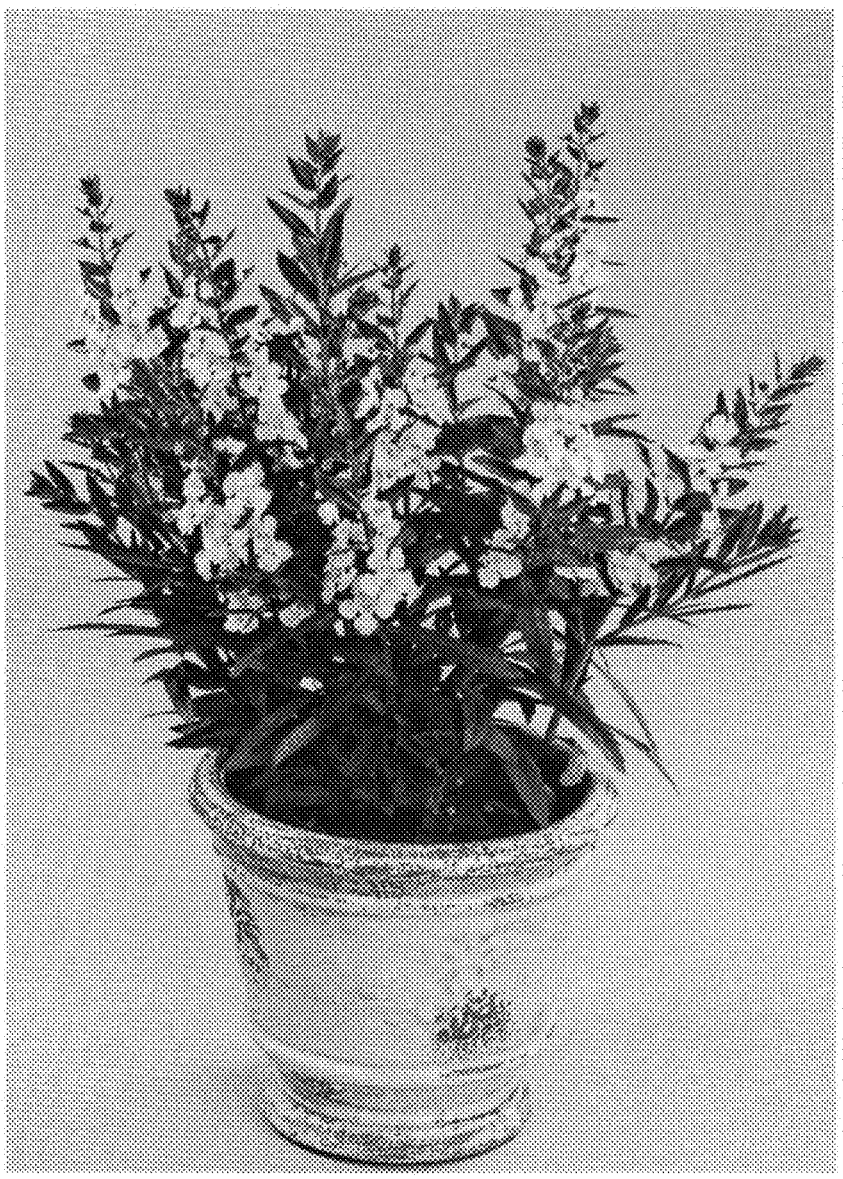

Latin name of the genus and species: *Angelonia angustifolia.*

Variety denomination: 'DALON12'.

BACKGROUND OF THE INVENTION

The new *Angelonia* cultivar is a product of a planned breeding program conducted by the inventor, Gavriel Danziger, in Moshav Mishmar Hashiva, Israel. The objective of the breeding program was to produce new *Angelonia* varieties for ornamental commercial applications. The cross resulting in this new variety was made during April of 2009.

The seed parent is the unpatented, proprietary seedling variety referred to as *Angelonia angustifolia* 'AL-497'. The pollen parent is the unpatented, proprietary seedling variety referred to as *Angelonia angustifolia* 'AL-671'. The new variety was discovered in October of 2010 by the inventor in a group of seedlings resulting from the 2009 crossing, in a research greenhouse in Moshav Mishmar Hashiva, Israel.

Asexual reproduction of the new cultivar has been performed by vegetative cuttings. This was first performed at a research greenhouse in Moshav Mishmar Hashiva, Israel in October of 2010 and has shown that the unique features of this cultivar are stable and reproduced true to type in successive generations.

SUMMARY OF THE INVENTION

The cultivar 'DALON12' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DALON12' These characteristics in combination distinguish 'DALON12' as a new and distinct Angelonia cultivar:

1. Upright plant habit.
2. Freely branching habit.
3. Freely flowering habit.
4. Large white colored flowers.
5. Good garden performance.

Plants of the new cultivar 'DALON12' are similar to plants of the seed parent, *Angelonia angustifolia* 'AL-497' in most horticultural characteristics, however, plants of the new cultivar 'DALON12' produce larger flowers than the seed parent. 'DALON12' also produces a white flower color compared to the blue flower of the seed parent.

Plants of the new cultivar 'DALON12' are similar to plants of the pollen parent; *Angelonia angustifolia* 'AL-671' in most horticultural characteristics, however, plants of the new cultivar 'DALON12' produce smaller flowers as well as a less vigorous growth habit than the pollen parent.

COMMERCIAL COMPARISON

Plants of the new cultivar 'DALON12' are comparable to the variety *Angelonia* 'DANGELONI4' U.S. Plant Pat. No. 19,451. The two *Angelonia* varieties are similar in most horticultural characteristics; however, the new variety 'DALON12' differs in producing larger flowers as well as more vigorous growth than the comparator.

Plants of the new cultivar 'DALON12' can also be compared to the commercial variety Angelonia 'DALON9' U.S. Plant Pat. No. 22,912. These varieties are similar in most horticultural characteristics; however 'DALON12' produces a white flower color and a more branched growth habit than the blue flowered 'DALON9'.

BRIEF DESCRIPTION OF THE PHOTOGRAPHS

The accompanying photograph in FIG. 1 illustrates in full color a typical plant of 'DALON12' grown in a greenhouse, in a 13 cm pot. Age of the plant photographed is approximately 9 weeks from a rooted cutting.

Figure 2:
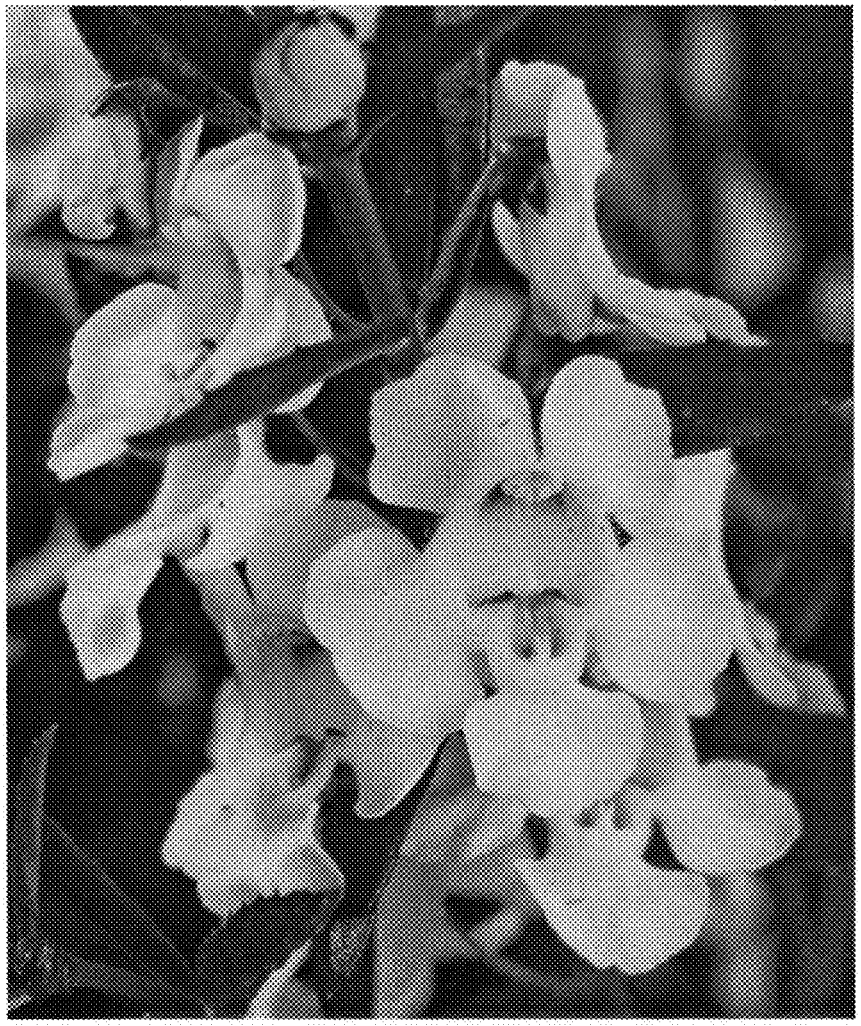

FIG. 2 illustrates in full color a close up of a typical bloom of 'DALON12'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DALON12' plants grown outdoors during, Spring, Summer, and Autumn in Moshav Mishmar Hashiva, Israel. The growing temperature ranged from 20° C. to 30° C. during the day and from 15° C. to 25° C. during the night. General light conditions are bright, normal sunlight. Measurements and numerical values represent averages of typical plant types.

Botanical classification: *Angelonia angustifolia* 'DALON12'.

PROPAGATION

Time to initiate roots: About 10 to 15 days at approximately 22° C.

Root description: Branched.

PLANT

Age of plant described: Approximately 70 days from rooted cutting.

Pot size of plant described: 13 cm.

Growth habit: Erect.

Pot size of plant described: 13 cm.

Height:

- *To top of foliage.*—30 cm.
- *To top of flowers.*—30 cm.

Plant spread: 30 cm.

Growth rate: Rapid.

Branching characteristics: Free branching.

Length of primary lateral branches: 30 cm.

Diameter of lateral branches: 0.5 cm.

Quantity of primary lateral branches: 6-8

Characteristics of primary lateral branches:

- *Form.*—Round.
- *Diameter.*—0.5 cm.
- *Color.*—Yellow-green group 144A RHS.
- *Texture.*—Smooth.
- *Strength.*—Breakable.

Internode length: 1.5-2 cm.

FOLIAGE

Leaf:

- *Arrangement.*—Opposite.
- *Quantity.*—Approximately 20-25 per branch.
- *Average length.*—2.5-9 cm.
- *Average width.*—1.5 cm.
- *Shape of blade.*—Lanceolate.
- *Apex.*—Rounded.
- *Base.*—Pointed.
- *Margin.*—Scalloped.
- *Texture of top surface.*—Smooth.
- *Appearance.*—Moderately glossy upper surface, matte lower surface.
- *Pubescence.*—No.
- *Aspect.*—50°.
- *Color.*—Young foliage upper side: Green group 137A RHS. Young foliage under side: Green group 137C RHS. Mature foliage upper side: Green group 137A RHS. Mature foliage under side: Green group 137C RHS.
- *Venation.*—Type: Pinnate. Venation color upper side: Green group 142C RHS. Venation color under side: Green group 144D RHS.
- *Petiole.*—No Petiole.

FLOWER

Natural flowering season: Approximately April through September in Israel.

Days to flowering from rooted cutting: 60.

Inflorescence and flower type and habit: Panicle.

Rate of flower opening: 4 to 14 days from bud to fully opened flower.

Flower longevity on plant: 5 days.

Persistent or self-cleaning: Self-Cleaning.

Bud:

- *Shape.*—Round.
- *Length.*—0.5 cm.
- *Diameter.*—0.5 cm.
- *Color.*—Yellow-green group 154D RHS.

Flower size:

- *Diameter.*—3 cm.
- *Length.*—2.5 cm.

Flower chamber:

- *Diameter.*—1.8 cm.
- *Length.*—1.8 cm.
- *Coloration.*—No striping or speckling. Near White 155D, flushed Yellow-Green 144C.

Flower pouch coloration: Near White 155D.

Nectary bulge coloration: Near White 155D.

Petals:

- *Length.*—1 cm.
- *Diameter.*—1.2 cm.
- *Quantity.*—5.
- *Texture.*—Smooth upper and lower surfaces.
- *Apex.*—Rounded.
- *Color.*—When opening: Upper surface: White group 155D RHS. Lower surface: White group 155D RHS. Fully opened: Upper surface: White group N999D RHS. Lower surface: White group N999D RHS.

Sepals:

- *Quantity per flower.*—5.
- *Shape.*—Ovate.

*Length.*—0.5 cm.
*Width.*—0.3 cm.
*Apex.*—Acute.
*Base.*—Stitched.
*Margin.*—Entire.
*Texture.*—Smooth.
*Color.*—Green group 143B RHS.

Peduncle: No true peduncle, panicle emerges as part of the plant stem.

Pedicel:
*Length.*—1.5-2 cm.
*Diameter.*—0.1 cm.
*Color.*—Yellow-green 145A RHS.

Fragrance: Faint, delicate scent.

REPRODUCTIVE ORGANS

Stamens:
*Number.*—4.
*Filament length.*—3 mm.

Anthers:
*Shape.*—Elliptic.
*Length.*—About 2 mm.
*Color.*—White group 155D RHS.

Pollen:
*Color.*—White group 155D RHS.
*Quantity.*—Moderate.

Pistil:
*Number.*—1.
*Length.*—0.3 cm.
*Style.*—Length: 0.4 cm. Color: Green group 142B RHS.
*Stigma.*—Shape: Thorn. Color: Green group 142B RHS.

OTHER CHARACTERISTICS

Seeds and fruits: If present, capsule 0.5 cm long with 50-75 seeds.

Disease/pest resistance: Neither resistance nor susceptibility to the normal diseases and pests of *Angelonia* have been observed. Pests common to *Angelonia* include Aphids and thrips. Typical diseases are *Botrytis* and *Pythium.*

Temperature tolerance: 5°-40° C.

What is claimed is:

1. A new and distinct cultivar of *Angelonia* plant named 'DALON12' as herein illustrated and described.

* * * * *